United States Patent
Taden et al.

(10) Patent No.: US 12,319,665 B2
(45) Date of Patent: *Jun. 3, 2025

(54) FUNCTIONALIZED α-ANGELICA LACTONE MONOMERS AND POLYMERS OBTAINED THEREFROM

(71) Applicant: Henkel AG & Co. KGaA, Duesseldorf (DE)

(72) Inventors: Andreas Taden, Duesseldorf (DE); Horst Beck, Neuss (DE); Adrian Brandt, Düsseldorf (DE); Kenji Ito, Duesseldorf (DE); Johannes Gerardus De Vries, Rostock (DE); Arianna Savini, Rostock (DE); Sergey Tin, Rostock (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 645 days.

This patent is subject to a terminal disclaimer.

(21) Appl. No.: 17/451,170

(22) Filed: Oct. 18, 2021

(65) Prior Publication Data
US 2022/0033370 A1    Feb. 3, 2022

Related U.S. Application Data

(63) Continuation of application No. PCT/EP2020/057055, filed on Mar. 16, 2020.

(30) Foreign Application Priority Data

Apr. 16, 2019  (EP) ..................... 19169508

(51) Int. Cl.
C08F 20/28 (2006.01)
C07D 307/58 (2006.01)

(52) U.S. Cl.
CPC ............ *C07D 307/58* (2013.01); *C08F 20/28* (2013.01)

(58) Field of Classification Search
CPC ........ C07D 307/58; C08F 20/28; C08G 63/08
See application file for complete search history.

(56) References Cited

FOREIGN PATENT DOCUMENTS

| | | | |
|---|---|---|---|
| JP | 53025553 A | * | 3/1978 |
| JP | S5325553 | | 3/1978 |

OTHER PUBLICATIONS

Schulte et al (Archiv der Pharmazie und . . . Gesellschaft; 292, abstract) (Year: 1959).*
STN Registry (Year: 1984).*
The machine translation into English of JP-53025553-A. (Year: 1978).*
V. E. Tarabanko and K. L. Kaygorodov, V E Tarabanko et al: "New Biodedradable Polymers Based on [alpha]-Angelicalactone", Chemistry for Sustainable Development p. 321-328Retrieved from the Internet:URL:https://www.sibran.ru/upload/iblock/f97/f97df118222b6c5bc83cd76c9164e116.pdf, https://www.sibran.ru/upload/iblock/f97/f97df118222b6c5bc83cd76c9164e116.pdf.
K. E. Schulte Und J. Reisch, Schulte K E et al: Beitrag zur Frage der Konstitution der [gamma]-Ketosäureamide [Constitution of .gamma.-oxo amides] p. 125-133 Archiv Der Pharmazie Und Berichte Der Deutschen Pharmazeutischen Gesellschaft, vol. 292, Jan. 1, 1959, Archiv Der Pharmazie Und Berichte Der Deutschen Pharmazeutischen Gesellschaft, vol. 292, Jan. 1, 1959, , Verlag Chemie, Weinheim.
Leo E. Manzer, Manzer L E Ed—Hisatomi Takashi et al: "Catalytic synthesis of @a-methylene-@c valerolactone: a biomass-derived acrylic monomer", pp. 249-256.
PCT International Search Report issued in connection with International Application No. PCT/EP2020/057055—mailed on Jun. 3, 2020.
K. E. Schulte et al., "Constitution of .gamma.-oxo amides", vol. 292, pp. 125-133 abstract (1959).

* cited by examiner

*Primary Examiner* — Karuna P Reddy
(74) *Attorney, Agent, or Firm* — Steven C. Bauman

(57) ABSTRACT

The present invention is directed to a monomer for chain growth polymerization, in particular anionic polymerization, said monomer having the general formula (EFL)

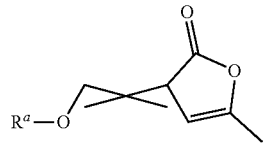

wherein: $R^a$ is a $C_1$-$C_{30}$ alkyl, $C_3$-$C_{30}$ cycloalkyl, $C_6$-$C_{18}$ aryl or $C_2$-$C_{12}$ alkenyl group. The present invention is further directed to a process for the anionic polymerization of at least one compound (EFL) as defined above, wherein said anionic polymerization is conducted in the presence of an initiator selected from the group consisting of: alkali metal organyls; alkali metal alkoxides; alkali metal thiolate; alkali metal amides; and compounds of an element of group 3a of the Periodic Table of the Elements. The process of anionic polymerization yields a homo- or co-polymer (p-EFL) having pendant lactone functional groups in its repeating units.

17 Claims, No Drawings

FUNCTIONALIZED α-ANGELICA LACTONE MONOMERS AND POLYMERS OBTAINED THEREFROM

FIELD OF THE INVENTION

The present invention is directed to functionalized α-angelica lactone compounds. More particularly, the present invention is directed to α-angelica lactones which are functionalized by an exo-cyclic alkoxymethylene group, to homo- and copolymers obtained from said functionalized α-angelica lactone compounds and to compositions based on said homo- or copolymers.

BACKGROUND OF THE INVENTION

Renewable resources, including materials derived from biological sources (biomass), present an important alternative to petrochemicals for use in many applications, in particular for use as raw materials in chemical and polymer synthesis. The exploitation of renewal resources provides a means to overcome problems with petrochemical supply, cost, environmental impact and sustainability. Furthermore, biologically derived materials can often be bio-compatible, bio-resorbable and/or biodegradable.

Levulinic acid (LA) is one of the top value-added chemicals that can be derived from renewable resources, as recognized in Bozell et al. *Technology Development for the Production of Biobased Products from Biorefinery Carbohydrides—the US Department of Energy's "Top 10" revisited*, Green Chem. 2010, 12, 539-554. Its use in the synthesis of a broad selection of molecules having potential industrial applications makes levulinic acid one of the most promising building blocks available from carbohydrates, as discussed in Werpy et al. *Top Value Added Chemicals for Bio-mass. Volume I—Results of Screening for Potential Candidates from Sugars and Synthesis Gas*, US Department of Energy (2004).

Having regard to levulinic acid derivatives, angelica lactones have received increasing attention in the last few years: their synthesis and applications were, for instance, recently summarized in Lima et al. *Angelica Lactones: from Biomass-Derived Plat-form Chemicals to Value-Added Products*, ChemSusChem 2018, 11, 25-47. This reference extensively covers the conversion of α-angelica lactone (α-AL) to γ-valerolactone and to other value-added chemicals, as well as the widespread use of α- and β-angelica lactones in conjugate addition reactions.

In Asaoka et al. *New Synthetic Method of 5- and 2,5-substituted 3-furoates and 1,4-dicarbonyl compounds from unsaturated lactones*, Chemistry Letters, pp. 171-174, 1977 Chemical Society of Japan, the title compounds were synthesized from 4-substituted 2-(1'-ethoxyalkylidene)-3-buten-4-olides 3 obtained by the reaction of 4-substituted 2- or 3-buten-4-olides with ortho esters and acetic anhydride.

As far as the successful polymerization of angelica lactones is concerned, only a very limited number of reports exist in the literature: one such report of which the present inventors are aware is Tarabanko et al. *New biodegradable polymers based on α-angelica lactone. Chem. Sustainable Develop* (2010), 18, pages 321-328. The reason for this paucity of literature may reside in the generally poor reactivity of five-membered lactones towards polymerization processes. In particular, the vinyl polymerization of angelica lactones for the synthesis of polymers which retain the lactone structure in their repeating unit appears to have been the object of only one publication, specifically Marvel et al. *The Structure of Vinyl Polymers. III. The Polymer from α-Angelica Lactone* (1939) 1682-1684. In this age-worn work, the authors described the formation of a low molecular weight polymer (Mw=800-900 Da)—obtained as a dark red solid—upon reaction of α-angelica lactone with catalytic amounts of boron trifluoride in carbon disulfide.

The incorporation of pendant lactone moieties into polymeric chains is recognized as having the potential to deliver materials with useful properties, in particular materials having high glass transition temperatures (Tg). However, such properties have to date only been realized for polymers obtained by reaction of functionalized γ-valerolactone and butyrolactone compounds. In this regard, the attention of the skilled reader may be directed to: Akkapeddi *Poly(a-methylene-y-butyrolactone) Synthesis, Configurational Structure, and Properties*, Macromolecules (1979) 546-551; Manzer *Catalytic synthesis of α-methylene-γ-valerolactone: a biomass-derived acrylic monomer*, Applied Catalysis A: General (2004) 272, 249-256; Vobecka et al. *Poly(a-methylene-g-valerolactone): Sustainable monomer synthesis and radical polymerization studies*, Polymer (2015) 74, 262-271; and, Gowda et al. *Sustainable Polymers from Biomass-Derived α-Methylene-γ-Butyrolactones*, In Encyclopedia of Polymer Science and Technology, 4$^{th}$ Ed., Mark, H. F., Ed.; Wiley: Hoboken, N.J., (2014) 8, 235-271.

To the best of the present inventors' knowledge, the use of α-angelica lactone to obtain high molecular weight polymers having pendant lactone groups has never been reported in the literature. The present invention has therefore focused upon this deficiency in the art to provide for polymers based upon functionalized α-angelica lactones, which polymers retain the lactone structure in their repeating unit.

STATEMENT OF THE INVENTION

In accordance with a first aspect of the invention there is provided a monomer for chain growth polymerization, preferably anionic polymerization, said monomer having the general formula (EFL)

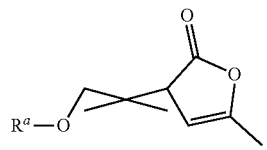

wherein: $R^a$ is a $C_1$-$C_{30}$ alkyl, $C_3$-$C_{30}$ cycloalkyl, $C_6$-$C_{18}$ aryl or $C_2$-$C_{12}$ alkenyl group.

The

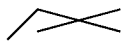

notation is used herein to indicate that all stereoisomers fall within the scope of this general formula (EFL). Said monomer may therefore have the following structure:

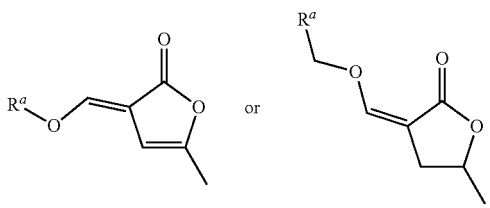

wherein, for instance, substituent $R^a$ of both said stereoisomers may be a $C_1$-$C_{18}$ alkyl, $C_3$-$C_{18}$ cycloalkyl, $C_6$-$C_{18}$ aryl or $C_2$-$C_{10}$ alkenyl group. For example, the present invention provides for a monomer (EFL) in which $R^a$ is ethyl (Et) and which is isolated as a crystalline solid at room temperature:

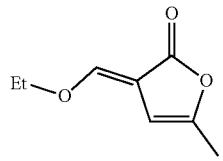

In an important embodiment of momomer (EFL), $R^a$ is a $C_1$-$C_{12}$ alkyl or $C_2$-$C_8$ alkenyl group, in particular a $C_1$-$C_6$ alkyl or $C_2$-$C_4$ alkenyl group. In a further embodiment, which is not intended to be mutually exclusive of that described above, said monomer (EFL) is characterized in that $R^a$ is a $C_3$-$C_6$ alkyl or $C_2$-$C_4$ alkenyl group.

In accordance with a second aspect of the present invention, there is provided a process for the synthesis of the monomer (EFL) as defined herein above and in the appended claims, said process comprising the step of reacting in the presence of an acid anhydride and an antioxidant:
α-angelica lactone; and,
an orthoester having the general formula (1)

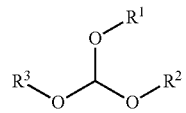

(1)

in which: $R^1$, $R^2$ and $R^3$ are independently selected from $C_1$-$C_{30}$ alkyl, $C_3$-$C_{30}$ cycloalkyl, $C_6$-$C_{18}$ aryl and $C_2$-$C_{12}$ alkenyl groups.

This synthetic process has been performed very effectively in embodiments wherein the acid anhydride is one of acetic anhydride, propionic anhydride, butyric anhydride or succinic anhydride and further wherein said acid anhydride is present in a molar excess to the total number of moles of reactants (a), b)). Equally, good results have been obtained where said antioxidant is present in an amount up to 10 wt. % based on the total weight of the reactants (a), b)) and, preferentially, comprises or consists of at least one sterically hindered phenol.

In accordance with a third aspect of the present invention, there is provided a process for chain growth polymerization of at least one monomer (EFL) as defined herein above and in the appended claims. In particular, there is provided a process for the anionic polymerization of at least one monomer (EFL) as defined herein above and in the appended claims, wherein said anionic polymerization is conducted in the presence of an initiator selected from the group consisting of: alkali metal organyls; alkali metal alkoxides; alkali metal thiolate; alkali metal amides; and, compounds of an element of group 3a of the Periodic Table of the Elements. To obtain a suitable yield of a homo- or co-polymer (p-EFL) having pendant lactone functional groups in its repeating units, it is preferred that this anionic polymerization process is performed at a temperature in the range from 50 to 150° C.

The present invention also provides for a homo- or co-polymer (p-EFL) which is obtainable by the process of chain growth polymerization and, in particular, by anionic polymerization as defined above and in the appended claims, which polymer (p-EFL) has the general formula:

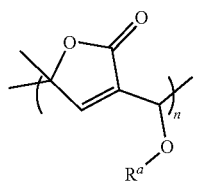

wherein: $R^a$ is a $C_1$-$C_{30}$ alkyl, $C_3$-$C_{30}$ cycloalkyl, $C_6$-$C_{18}$ aryl or $C_2$-$C_{12}$ alkenyl group; and,
n is an integer of at least 20.

The polymer (p-EFL) having pendant lactone functional groups in its repeating units, which is obtainable or obtained by the process of anionic polymerization as defined herein above and in the appended claims, should be characterized by at least one of: i) a number-average molecular weight (Mn), as determined as measured by gel permeation chromatography (GPC) in tetrahydrofuran using a polystyrene standard, of at least 2500 g/mol, preferably from 10000 to 150000 g/mol; ii) a glass transition temperature (Tg) of from 50 to 200° C., preferably from 100 to 200° C.; and, iii) a polydispersity index (PDI) of from 1.1 to 2.0, preferably from 1.10 to 1.80.

Said polymer (p-EFL) having pendant lactone functional groups in its repeating units may find utility as a macro-monomer in the ring-opening polymerization of at least one further monomer selected from the group consisting of: cyclic carbonates; cyclic anhydrides; oxalates; and cyclic esters having 5-, 6-, and/or 7-member rings. Alternatively, said polymer (p-EFL) having pendant lactone functional groups may find utility as a macro-monomer in an esterification reaction with at least two co-monomers which are capable of forming an ester bond.

The present invention also provides for the use of the homo- or copolymer (p-EFL) having pendant lactone functional groups as defined herein above and in the appended claims as a curable, crosslinkable or otherwise reactive component of a coating composition, a sealant composition or an adhesive composition. Such a composition may, in an important embodiment, be defined as having two separate, reactive components that when mixed together form a reactive mixture that undergoes curing or hardening, said two-component composition comprising: i) in a first component, said polymer (p-EFL) as defined herein above and in the appended claims; and ii) in a second component, an un-substituted or hydroxyl-substituted mono-, di- or trialkylamines.

DEFINITIONS

As used herein, the singular forms "a", "an" and "the" include plural referents unless the context clearly dictates otherwise.

The terms "comprising", "comprises" and "comprised of" as used herein are synonymous with "including", "includes", "containing" or "contains", and are inclusive or open-ended and do not exclude additional, non-recited members, elements or method steps. If used, the phrase "consisting of" is closed and excludes all additional elements. Further, the phrase "consisting essentially of" excludes additional material elements but allows the inclusion of non-material elements that do not substantially change the nature of the invention.

When amounts, concentrations, dimensions and other parameters are expressed in the form of a range, a preferable range, an upper limit value, a lower limit value or preferable upper and limit values, it should be understood that any ranges obtainable by combining any upper limit or preferable value with any lower limit or preferable value are also specifically disclosed, irrespective of whether the obtained ranges are clearly mentioned in the context.

The words "preferred", "preferably", "desirably" and "particularly" are used frequently herein to refer to embodiments of the disclosure that may afford particular benefits, under certain circumstances. However, the recitation of one or more preferable, preferred, desirable or particular embodiments does not imply that other embodiments are not useful and is not intended to exclude those other embodiments from the scope of the disclosure.

As used throughout this application, the word "may" is used in a permissive sense—that is meaning to have the potential to—rather than in the mandatory sense.

As used herein, "ambient conditions" refers to a set of parameters that include temperature, pressure and relative humidity of the immediate surroundings of the element in question. Herein ambient conditions are: a relative humidity of from 30 to 100% percent; a temperature in the range from 20 to 40° C.; and, a pressure of 0.9 to 1.1 bar.

As used herein "room temperature" is 23° C.±2° C.

As used herein, the terms "monomer" and "co-monomer" refer to a molecule that is capable of conversion to polymers, synthetic resins or elastomers by combination with itself or other similar molecules or compounds. The terms are not limited to small molecules but include oligomers, polymers and other large molecules capable of combining with themselves or other similar molecules or compounds.

As used herein, "macro-monomer" refers to a polymer having at least one functional group through which polymerization reactions can proceed. Macro-monomers are thus macromolecular monomers which can be converted to homo- or copolymers of defined structures. It is not precluded that a macro-monomer as used herein comprises more than one polymeric chain attached to one functional group.

As used herein, "polymerization conditions" are those conditions that cause the at least one monomer to form a polymer, such as temperature, pressure, atmosphere, ratio of starting components used in the polymerization mixture, reaction time, or external stimuli of the polymerization mixture. The polymerization process can be carried out in bulk, or solution, or other conventional polymerization modes. The process is operated at any of the reaction conditions appropriate to the polymerization mechanism.

The term "chain-growth polymerization" as used herein refers to the mechanism defined in the work "*Polymer Chemistry*", Ninth Edition, Charles E. Carraher, Jr., pages 159 to 161. Chain-growth polymerization is also called addition polymerization and is based on free-radical, cationic, anionic and coordination reactions where a single initiating species causes the growth of a polymer chain. In chain-growth polymerization, an activated species such as an initiator adds one monomer molecule to create a new active center, which again adds another monomer molecule to create another active center and so on, so that the chain growth proceeds as a chemical chain reaction.

The term "anionic polymerization" as used herein refers to the mechanism defined in the work "*Advanced Organic Chemistry*", Third Edition, Jerry March, pages 151 to 161. Specifically, it refers to an ionic polymerization in which the kinetic chain carriers are anions. Accordingly, an anionic polymerization reaction is a chain reaction in which the growth of the polymer chain proceeds by reaction(s) between the monomer(s) and the reactive site(s) on the polymer chain with regeneration of the reactive site(s) at the end of each growth step. Herein the anionic polymerization is used to produce macromolecules from monomers that contain a carbon-carbon double bond. The polymerizations are initiated by nucleophilic addition to the double bond of the monomer, wherein the initiator comprises an anion, such as hydroxide, alkoxides, cyanide, or a carbanion.

As used herein, the term "ring-opening polymerization" denotes a polymerization in which a cyclic compound (monomer) is opened to form a linear polymer in the presence of an appropriate catalyst. The reaction system tends towards an equilibrium between the desired resulting high-molecular compounds, a mixture of cyclic compounds and/or linear oligomers, the attainment of which equilibrium largely depends on the nature and amount of the cyclic monomers, the catalyst used and on the reaction temperature. The use of solvents and/or emulsions in the polymerization is not recommended as their removal once the reaction is complete can be complex. That aside, an instructive disclosure of ring-opening polymerization may be found in inter alia Nuyken et al., *Ring-Opening Polymerization—An Introductory Review* Polymers 2013, 5, 361-403.

The term "orthoester" as used herein relates to compounds comprising a carbon atom linked to three alkoxy groups.

The name α-angelica lactone (CAS 591-12-8) is used synonymously with 5-methyl-3H-furan-2-one.

The term "exo" is being used in accordance with its standard definition in the art.

As used herein, "$C_1$-$C_n$ alkyl" group refers to a monovalent group that contains 1 to n carbons atoms, that is a radical of an alkane and includes straight-chain and branched organic groups. As such, a "$C_1$-$C_{30}$ alkyl" group refers to a monovalent group that contains from 1 to 30 carbons atoms, that is a radical of an alkane and includes straight-chain and branched organic groups. Examples of alkyl groups include, but are not limited to: methyl; ethyl; propyl; isopropyl; n-butyl; isobutyl; sec-butyl; tert-butyl; n-pentyl; n-hexyl; n-heptyl; and, 2-ethylhexyl. In the present invention, such alkyl groups may be unsubstituted or may be substituted with one or more substituents such as halo, nitro, cyano, amido, amino, sulfonyl, sulfinyl, sulfanyl, sulfoxy, urea, thiourea, sulfamoyl, sulfamide and hydroxy. The halogenated derivatives of the exemplary hydrocarbon radicals listed above might, in particular, be mentioned as examples of suitable substituted alkyl groups. In general, however, a preference for unsubstituted alkyl groups containing from 1-18 carbon atoms ($C_1$-$C_{18}$ alkyl)—for example unsubstituted alkyl groups containing from 1 to 12 carbon atoms ($C_1$-$C_{12}$ alkyl)—should be noted.

The term "$C_3$-$C_{30}$ cycloalkyl" is understood to mean a saturated, mono-, bi- or tricyclic hydrocarbon group having from 3 to 30 carbon atoms. In general, a preference for cycloalkyl groups containing from 3-18 carbon atoms ($C_3$-

$C_{18}$ cycloalkyl groups) should be noted. Examples of cycloalkyl groups include: cyclopropyl; cyclobutyl; cyclopentyl; cyclohexyl; cycloheptyl; cyclooctyl; adamantane; and norbornane.

As used herein, an "$C_6$-$C_{18}$ aryl" group used alone or as part of a larger moiety—as in "aralkyl group"—refers to optionally substituted, monocyclic, bicyclic and tricyclic ring systems in which the monocyclic ring system is aromatic or at least one of the rings in a bicyclic or tricyclic ring system is aromatic. The bicyclic and tricyclic ring systems include benzofused 2-3 membered carbocyclic rings. Exemplary aryl groups include: phenyl; indenyl; naphthalenyl, tetrahydronaphthyl, tetrahydroindenyl; tetrahydroanthracenyl; and, anthracenyl. And a preference for phenyl groups may be noted.

As used herein, "$C_2$-$C_{12}$ alkenyl" refers to hydrocarbyl groups having from 2 to 12 carbon atoms and at least one unit of ethylenic unsaturation. The alkenyl group can be straight chained, branched or cyclic and may optionally be substituted. The term "alkenyl" also encompasses radicals having "cis" and "trans" configurations, or alternatively, "E" and "Z" configurations, as appreciated by those of ordinary skill in the art. In general, however, a preference for unsubstituted alkenyl groups containing from 2 to 10 ($C_{2-10}$) or 2 to 8 ($C_{2-8}$) carbon atoms should be noted. Examples of said $C_2$-$C_{12}$ alkenyl groups include, but are not limited to: —CH=$CH_2$; —CH=$CHCH_3$; —$CH_2CH$=$CH_2$; —C(=$CH_2$)($CH_3$); —CH=$CHCH_2CH_3$; —$CH_2CH$=$CHCH_3$; —$CH_2CH_2CH$=$CH_2$; —CH=C($CH_3$)$_2$; —$CH_2C$(=$CH_2$)($CH_3$); —C(=$CH_2$)$CH_2CH_3$; —C($CH_3$)=$CHCH_3$; —C($CH_3$)CH=$CH_2$; —CH=$CHCH_2CH_2CH_3$; —$CH_2CH$=$CHCH_2CH_3$; —$CH_2CH_2CH$=$CHCH_3$; —$CH_2CH_2CH_2CH$=$CH_2$; —C(=$CH_2$)$CH_2CH_2CH_3$; —C($CH_3$)=$CHCH_2CH_3$; —CH($CH_3$)CH=$CHCH$; —CH($CH_3$)$CH_2CH$=$CH_2$; —$CH_2CH$=C($CH_3$)$_2$; 1-cyclopent-1-enyl; 1-cyclopent-2-enyl; 1-cyclopent-3-enyl; 1-cyclohex-1-enyl; 1-cyclohex-2-enyl; and, 1-cyclohexyl-3-enyl.

As used herein, "alkylaryl" refers to alkyl-substituted aryl groups and "substituted alkylaryl" refers to alkylaryl groups further bearing one or more substituents as set forth above.

The term "hetero" as used herein refers to groups or moieties containing one or more heteroatoms, such as N, O, Si and S. Thus, for example "heterocyclic" refers to cyclic groups having, for example, N, O, Si or S as part of the ring structure. "Heteroalkyl" and "heterocycloalkyl" moieties are alkyl and cycloalkyl groups as defined hereinabove, respectively, containing N, O, Si or S as part of their structure.

As used herein, the term "catalytic amount" means a sub-stoichiometric amount of catalyst relative to a reactant, except where expressly stated otherwise.

The term "Lewis acid" used herein denotes any molecule or ion—often referred to as an electrophile—capable of combining with another molecule or ion by forming a covalent bond with two electrons from the second molecule or ion: a Lewis acid is thus an electron acceptor.

The molecular weights referred to in this specification can be measured with gel permeation chromatography (GPC) using polystyrene calibration standards, such as is done according to ASTM 3536.

The term "polyol" as used herein shall include diols and higher functionality hydroxyl compounds.

As used herein, "crystalline" refers to a solid having a highly regular chemical structure. In particular, a crystalline compound may be produced as one or more single crystalline form—polymorph or pseudopolymorph—thereof. Particles of a crystalline solid may be presented as any combination of single crystals, aggregates and agglomerates.

Where mentioned, a calculated glass transition temperature ("Tg") of a polymer or co-polymer is that temperature which may be calculated by using the Fox equation (T. G. Fox, Bull. Am. Physics Soc., Volume 1, Issue No. 3, page 123 (1956)). The glass transition temperatures of certain homo-polymers may be found in the published literature, such as in "*Polymer Handbook*", edited by J. Brandrup and E. H. Immergut, Interscience Publishers.

The actual glass transition temperature (Tg) of a polymer can be determined by differential scanning calorimetry (DSC). The use of DSC to determine Tg is well known in the art and is described by B. Cassel and M. P. DiVito in "*Use of DSC To Obtain Accurate Thermodynamic and Kinetic Data*", American Laboratory, January 1994, pp 14-19, and by B. Wunderlich in Thermal Analysis, Academic Press, Inc., 1990. The glass transition temperatures (Tg) specifically measured in the current patent application have been measured according to the methodology of Deutsches Institut fur Normung (DIN) 11357.

The term "anhydrous" is intended to mean herein that the applicable reaction mixture or component comprises less than 0.25 wt. % of water, based on the weight of the mixture or component. The term "essentially free of solvent" should be interpreted analogously as meaning the relevant composition comprises less than 0.25 wt. % of solvent.

DETAILED DESCRIPTION OF THE INVENTION

Synthesis of the Functionalized α-Angelica Lactone (EFL)

The synthesis of the functionalized α-angelica lactone (EFL) is most broadly characterized by the following reaction scheme:

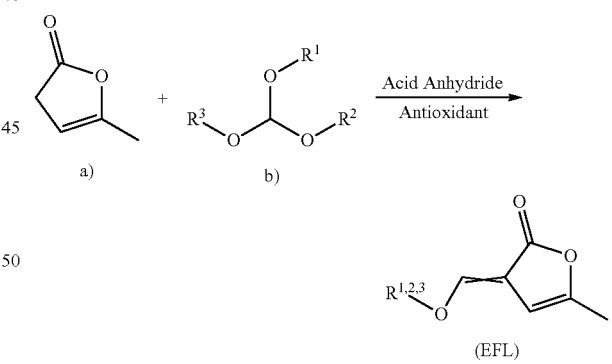

There is no particular intention to limit the means by which the reactant alpha-angelica lactone (a)) is obtained: aside from said compound being commercially available, it may also be synthesised via a multiplicity of synthesis routes known to the skilled artisan. Reference in this regard might be made to http://www.molbase.com/en/synthesis_591-12-8-moldata-4778.html. When expedient based on the synthesis route employed, the alpha-angelica lactone may be isolated and purified using methods known in the art. Mention in this regard may be made of extraction, evaporation, distillation and chromatography as suitable techniques.

The orthoester reactants having utility in the above described reaction scheme have the general formula (b)) herein below:

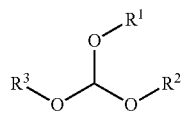

in which: $R^1$, $R^2$ and $R^3$ are independently selected from $C_1$-$C_{30}$ alkyl, $C_3$-$C_{30}$ cycloalkyl, $C_6$-$C_{18}$ aryl and $C_2$-$C_{12}$ alkenyl groups.

In a preferred embodiment of the orthoesters of Formula (b)), $R^1$, $R^2$ and $R^3$ are independently selected from $C_1$-$C_{18}$ alkyl and $C_2$-$C_{12}$ alkenyl groups; $R^1$, $R^2$ and $R^3$ may for instance be independently selected from $C_1$-$C_{12}$ alkyl groups and $C_2$-$C_8$ alkenyl groups or independently selected from $C_1$-$C_6$ alkyl or $C_2$-$C_4$ alkenyl groups. Alternatively or additionally to the aforementioned embodiment, it is preferred that at least two of $R^1$, $R^2$ and $R^3$ in Formula (1) are the same.

Examples of suitable orthoesters (b)) for use in the present invention include but are not limited to: triethyl orthoformate ($R^1$=$R^2$=$R^3$=Et); trimethyl orthoformate ($R^1$=$R^2$=$R^3$=Me); tributyl orthoformate ($R^1$=$R^2$=$R^3$=Bu); tripropoxy orthoformate ($R^1$=$R^2$=$R^3$=nPr); diethyl vinyl orthoformate ($R^1$=$R^2$=Et, $R^3$=CH$_2$=CH$_2$); trioctadecyl orthoformate ($R^1$=$R^2$=$R^3$=$C_{18}H_{37}$); and, tripentyl orthoformate ($R^1$=$R^2$=$R^3$=$C_5H_{11}$).

As noted in the above scheme, the reaction is performed in the presence of an acid anhydride. Typically said acid anhydride is one of acetic anhydride, propionic anhydride, butyric anhydride or succinic anhydride. A preference for acetic anhydride is noted. That aside, the acid anhydride should be present in a catalytic amount which, in this regard, may include sub-stoichiometric amounts of said acid anhydride relative to the total number of moles of reactants (a), b)) but does not preclude the acid anhydride being present in molar excess—for instance up to a 20% molar excess—to the total number of moles of reactants (a), b)).

The reaction is also performed in the presence of a suitable antioxidant which will typically constitute up to 10 wt. % or up to 5 wt. %, based on the total weight of the reactants (a), b)) The use of one or more sterically hindered phenol—including but not limited to 2,6-di-tert-butyl-4-methylphenol (BHT) and/or butylated hydroxyanisole (BHA)—is preferred herein.

Whilst the presence of a co-catalyst is not required, it is also not precluded. The reaction between the orthoester and the alpha-angelica lactone may, in an embodiment, be performed in the presence of a catalytic amount of a strong protic acid selected from a group consisting of $H_2SO_4$, $HNO_3$, HCl, HBr, HI, trifluoroacetic acid (TFA), $H_3PO_4$, p-toluene sulfonic acid (p-TSA) and methanesulfonic acid (MSA).

The above reaction should be performed under anhydrous conditions. Exposure to atmospheric moisture may be avoided by providing the reaction vessel with an inert, dry gaseous blanket. Whilst dry nitrogen, helium and argon may be used as blanket gases, precaution should be used when common nitrogen gases are used as a blanket, because such nitrogen may not be dry enough on account of its susceptibility to moisture entrainment; the nitrogen may require an additional drying step before use herein.

The above described reaction may be carried out in the presence of a solvent. Inert solvents are preferred as solvents; these contain no reactive groups that react with the starting compounds. Inert, polar, aprotic solvents are particularly preferred. Named as such are, e.g., cyclic ether compounds, in particular tetrahydrofuran (THF).

The reaction temperature is typically at least 40° C. and preferably at least 60° C. Whilst the reaction temperature may be 200° C. or higher, it is preferred that the temperature does not exceed 190° C. or even 180° C. in order inter alia: to maintain workable reactor pressures; and, where applicable, to maintain adequate catalyst activity without deactivating or decomposing the catalyst. As the reaction is generally exothermic, some cooling might be required as it progresses.

The process pressure is not critical: as such, the reaction can be run at sub-atmospheric, atmospheric, or super-atmospheric pressures but pressures at or slightly above atmospheric pressure are preferred. Mention in this regard may be made of pressures of from 100 to 500 MPa or from 100 to 200 MPa.

The progress of the above reaction can be monitored by known tecchniques. For example, samples may be withdrawn from the reaction vessel and tested using Gas Chromatography (GC) with Flame Ionization Detection (FID).

The reaction product may be isolated and purified using methods known in the art. Whilst mention in this regard may be made of extraction, filtration, evaporation, distillation and chromatography as suitable techniques it is most convenient that the product of the reaction be isolated by distilling off the solvent and any unreacted starting materials.

The Formation of Exo-Methylene Functionalized Polymers

The second aspect of the present invention provides for the polymerization of the above defined monomeric compounds (EFL). Broadly, the polymerization is performed by means of chain growth polymerization but may, in particular, be performed under anionic conditions: the skilled artisan will select appropriate conditions so that the vinyl-addition pathway of polymerization predominates over the competing ring-opening polymerization pathway. The resultant homo- or copolymer (p-EFL) thus retains the lactone structure in its repeating unit.

Co-Monomers

As mentioned previously, the aforementioned monomers (EFL) may be incorporated into co-polymers (p-EFL). Most broadly, viable co-monomers are those that provide reasonable polymerization reaction rates under suitable, pragmatic anionic polymerization conditions.

In a non-limiting and illustrative embodiment of the present invention, there is provided a copolymer (p-EFL) comprising:

from 15 to 75 wt. %, preferably from 15 to 60 wt. % of at least one monomer as defined in Formula (EFL) hereinabove; and, from 25 to 85 wt%, preferably from 40 to 85 wt. % of at least one co-monomer.

In a further exemplary embodiment—which is not intended to be mutually exclusive of the above illustrative embodiment—a copolymer is derived from the above defined monomer (EFL) and at least one further monomer, wherein said at least one further monomer is a non-carbonyl-providing, olefinically unsaturated monomer selected from the group consisting of: (meth)acrylonitrile; alkyl (meth) acrylate esters; (meth)acrylic acids; vinyl esters; and vinyl monomers.

Suitable vinyl monomers include: 1,3-butadiene; isoprene; styrene; divinyl benzene; heterocyclic vinyl compounds; and vinyl halides such as chloroprene. Preferably the vinyl monomers include ethylene, styrene, butadiene and isoprene. Suitable vinyl esters include vinyl acetate, vinyl propionate, vinyl versatate and vinyl laurate.

Suitable alkyl esters of acrylic acid and methacrylic acid are those derived from $C_1$ to $C_{14}$ alcohols and thereby include as non-limiting examples: methyl acrylate; methyl methacrylate; ethyl acrylate; ethyl methacrylate; n-butyl acrylate; n-butyl methacrylate; 2-ethylhexyl acrylate; 2-ethylhexyl methacrylate; isopropyl acrylate; hydroxyethyl methacrylate; hydroxypropyl methacrylate; isopropyl methacrylate; n-propyl acrylate; n-propyl methacrylate; and, di(meth)acrylate esters of alkane diols such as 1,6-hexane diol diacrylate.

Polymerization Processes

The anionic polymerization of the monomers (EFL) and any co-monomers present is conducted in the presence of an initiator selected from the group consisting of: alkali metal organyls; alkali metal alkoxides; alkali metal thiolate; alkali metal amides; and, compounds of an element of group 3a of the Periodic Table of the Elements, preferably an aluminum or boron organyl.

Alkali metal organyls which may be used are mono-, bi- or multifunctional alkali metal alkyls, aryls or aralkyls. It is advantageous to use organolithium compounds including but not limited to: ethyllithium; propyllithium; isopropyllithium; n-butyllithium; sec-butyllithium; tert-butyllithium; phenyllithium; diphenylhexyllithium; hexamethylenedilithium; butadienyllithium; isoprenyllithium; polystyryllithium; 1,4-dilithiobutane; 1,4-dilithio-2-butene; and, 1,4-dilithiobenzene.

Alkali metal alkoxides which may be used, either alone or in admixture, are aliphatic, aromatic or araliphatic alkoxides of lithium, sodium or potassium. Examples are lithium, sodium or potassium methoxide, ethoxide, n-propoxide, isopropoxide, n-butoxide, sec-butoxide, tert-butoxide, n-pentoxide, isopentoxide, hexoxide, amyl alkoxide, 3,7-dimethyl-3-octoxide, phenoxide, 2,4-di-tert-butylphenoxide, 2,6-di-tert-butylphenoxide, 3,5-di-tert-butylphenoxide, 2,4-di-tert-butyl-4-methylphenoxide and trimethylsilanoate. Preference is given to using the aliphatic alkoxides in particular methoxides, ethoxides, n-propoxides, isopropoxides, n-butoxides, sec-butoxides and tert-butoxides of sodium, potassium or lithium.

Alkali metal thiolates which may be used, either alone or in admixture, are aliphatic, aromatic or araliphatic thiolates of lithium, sodium or potassium. Examples are lithium, sodium or potassium methyl sulfide, ethyl sulfide, butyl sulfide, hexyl sulfide, decyl sulfide, dodecyl sulfide, stearyl sulfide, thiophenoxide, tolyl sulfide, cyclohexyl sulfide or dilithium 1,2-dimercaptoethane. Preference is given to aliphatic thiolates having from 8 to 18 carbon atoms in the alkyl chain.

Alkali metal amides which may be used, either alone or in admixture, are lithium, sodium or potassium salts of ammonia or primary or secondary amines having aliphatic, aromatic or araliphatic substituents. Examples of suitable amides are lithiumamide, N-lithiummethylamide, N-lithiumethylamide, N-lithiumpropylamide, N-lithiumbutylamide, N-lithiumamylamide, N-lithiumphenylamide or the corresponding sodium or potassium salts; N-lithiumdimethylamide, N-lithiumdiethylamide, N-lithiumdipropylamide, N-lithiumdibutylamide, N-lithiumdiamylamide, N-lithium-(N,N-bis-trimethylsilyl)amide, N-lithiumdicyclohexylamide, N-lithium-N-methylanilide, N-lithium-N-ethylanilide, N-lithiummorpholide, N-lithiumdiphenylamide, N-lithiumpiperidide or N-lithiumimidazolide. Particular preference is given to salts of secondary aliphatic amines, with very particular preference being given to N-lithiumdiisopropylamide.

Aluminum or boron organyls which may be used are those of the formula $R_3Al$ or $R_3B$, wherein the radicals R are each, independently of one another, hydrogen, halogen, C1-C18-alkyl or C6-C18-aryl. Preferred aluminum organyls are aluminum trialkyls such as trimethylaluminum, triethylaluminum, triisobutylaluminum, tri-n-butylaluminum, triisopropylaluminum, tri-n-hexylaluminum, diethylaluminum hydride, diisobutylaluminum hydride or isoprenylaluminum. Particular preference is given to using triisobutylaluminum.

It is envisaged that it may be possible to use aluminum organyls which are formed by the partial or complete hydrolysis, alcoholysis, aminolysis, thiolysis, phosphinolysis or oxidation of alkyl- or arylaluminum compounds or those which are complexed with alkoxides, thiolates, sulfides, amides, imides, nitrides or phosphides. Examples of such compounds carrying hetero substituents include but are not limited to: diethylaluminum N,N-dibutylamide; diethylaluminum ethoxide; diisobutylaluminum ethoxide; diisobutyl-(2,6-di-tert-butyl-4-methyl-phenoxy)aluminum; methylaluminoxane; isobutylated methylaluminoxane; isobutylaluminoxane; tetraisobutyldialuminoxane; bis(diisobutyl)aluminum oxide; diethylboron methoxide; trimethylboroxine; and, 2-phenyl-1,3,2-dioxaborinane.

Further examples of suitable initiators include: aluminum alkoxides, such as aluminum trimethoxide, aluminum triethoxide, aluminum tripropoxide, and, aluminum tributoxide; and, boric acid trialkyl esters. Preference is given to using the aluminum compounds, especially those having oxo or alkoxide groups. Very particular preference is given to using diethylaluminum ethoxide, diisobutylaluminum ethoxide, methyl aluminoxane, aluminum propoxide and aluminum tri-sec-butoxide.

There is no particular limitation on the amount of initiator used but it will be typically be from 0.0001 to 5 parts by weight, and preferably from 0.05 to 1 part by weight, based on 100 parts by weight of the monomers.

Furthermore, the polymerization may be performed in solution or in the melt without a solvent. When used, suitable solvents for the polymerization should be non-reactive, organic liquids capable of dissolving at least 1 wt. % and preferably over 10 wt. % polymers at 25° C. Dichloromethane and tetrahydrofuran (THF) may be mentioned as exemplary solvents.

In certain embodiments, the anionic polymerization process is performed in the presence of a Lewis acid. The preferred Lewis acids for use in the polymerization processes of the present invention are characterized as being "non-protic": they are Lewis acids which are not capable of functioning as a source of a proton (H+). Particularly preferred Lewis acids for the purposes of this invention include halides of elements selected from the group consisting of aluminum, manganese, iron, cobalt, boron, iron, titanium, tin, chromium, magnesium, vanadium, hafnium, zirconium and zinc.

In the homo- and co-polymerization processes of the present invention, the amount of (non-protic) Lewis acid should be adjusted such that the activity of the catalyst, as measured by the weight of monomer reacted per unit of time at a given temperature, does not decrease more than 20% as compared to the catalyst activity under the same conditions in the absence of Lewis acid: in this regard it will often be advantageous to utilize a Lewis acid: catalyst weight ratio in the range of from 0.1 to 1.0.

Whilst there is certainly no intention to preclude either batch-wise or continuous performance of the polymerization—as described in U.S. Pat. Nos. 5,777,177 and 5,689,012—the polymerization reactions are most suitably performed as semi-batch processes.

The polymerization reaction can be performed in any type of vessel that is suitable for the pressures and temperatures described below. In the preferred semi-batch process, the vessel should have one or more inlets through which monomer(s) can be introduced during the reaction. In the less desired continuous process, a reactor vessel should contain at least one outlet through which a portion of the partially polymerized reaction mixture could be withdrawn. That aside, exemplary vessels for continuous or semi-batch operations include but are not limited to: tubular reactors; loop reactors; and, continuous stirred tank reactors (CTSR). Any reactor should, of course, be equipped with a means for providing or removing heat so that the temperature of the polymerization mixture can be maintained within the desired range: there is no intention to limit such means but examples include jacketing for thermal fluids and internal and/or external heaters.

At the commencement of the polymerization process, the initiator and, optionally, a Lewis acid are charged into the reaction vessel. In the preferred semi-batch process, the initiator may undergo a preliminary heating step, in the absence of monomer(s), at a temperature of from 50 to 220° C., for instance from 75 to 180° C. That preliminary heating step is conducted in an inert atmosphere and is typically but, not necessarily, conducted under sub-atmospheric pressure. The preliminary heating is, moreover, usually conducted for a period of at least 10 minutes: a period of from 10 to 30 minutes might be mentioned for illustrative purposes.

The homo-polymerization of monomers (EFL), the copolymerization of two or more monomers meeting the general formula (EFL), and the co-polymerization of monomers (EFL) with co-monomers should be performed under anhydrous conditions and in the absence of any compound having an active hydrogen atom, save for the deliberate inclusion of the initiating compound. Exposure to atmospheric moisture may be avoided by providing the reaction vessel with an inert, dry gaseous blanket. Whilst dry nitrogen, helium and argon may be used as blanket gases, precaution should be used when common nitrogen gases are used as a blanket, because such nitrogen may not be dry enough on account of its susceptibility to moisture entrainment; the nitrogen may require an additional drying step before use herein.

The polymerization temperature is typically at least 25° C. and preferably at least 50° C. Whilst the reaction temperature may be 200° C. or higher, it is preferred that the temperature does not exceed 200° C., 175° C. or even 150° C. in order inter alia: to maintain workable reactor pressures; to minimize the rate of polymer degradation and the concomitant formation of volatile impurities or other by-products; and, if applicable, to maintain adequate catalyst activity without deactivating or decomposing the catalyst. Within the typically desired polymerization temperature range of from 50 to 150° C., the solvent type, agitation rate and pressure will be determinative of the reaction times but times of from 1 to 100 hours will be standard.

The process pressure is not critical: as such, the polymerization reaction can be run at sub-atmospheric, atmospheric, or super-atmospheric pressures but pressures at or slightly above atmospheric pressure are preferred. Mention in this regard may be made of pressures of from 100 to 500 MPa or from 100 to 200 MPa.

The reaction product may be isolated and purified using methods known in the art. Whilst mention in this context may be made of extraction, evaporation, distillation and chromatography as suitable techniques, it is most convenient that the product of the reaction be isolated by distilling off the solvent and any un-reacted starting materials under reduced pressure.

Where it is intended that the (optionally purified) reaction product be stored upon production, the polymers should be disposed in a vessel with an airtight and moisture-tight seal.

The homo- or copolymers (p-EFL) derived in the above described polymerization processes may possess: i) a number-average molecular weight (Mn), as determined by gel permeation chromatography (GPC) in tetrahydrofuran using a polystyrene standard, of at least 2500 g/mol, for instance from 10000 to 150000 g/mol and preferably from 10000 to 100000 g/mol; ii) a glass transition temperature (Tg) of from 50 to 200° C., for example from 100 to 200° C.; and, iii) a polydispersity index (PDI) of from 1.1 to 2.0, for example from 1.10 to 1.90, and preferably from 1.10 to 1.80.

Polymer Derivatives of the Homo- And Co-Polymers (P-EFL)

i) Ring-Opening Polymerization

The lactone functional group in the polymers (p-EFL) of the present invention can be used to regulate the ring opening polymerization of at least one monomer selected from the group consisting of: cyclic carbonates; cyclic anhydrides; oxalates; and, cyclic esters having 5-, 6-, and/or 7-member rings. In particular, the polymers (p-EFL) may be present as a reactant macro-monomer in a ring open polymerization with at least one monomer selected from the group consisting of: lactide; glycolide; ε-caprolactone; para-dioxanone; trimethylene carbonate; 1,4-dioxepan-2-one; 1,5 dioxepan-2-one; γ-butyrolactone; α-methylene-γ-butyrolactone; γ-methyl-α-methylene-γ-butyrolactone; α-bromo-γ-butyrolactone; α-hydroxy-γ-butyrolactone; α-acetyl-γ-butyrolactone; spirocyclic-γ-butyrolactone; γ-valerolactone; α-angelica lactone; and β-angelica lactone. The derived copolymer may be a block copoly(ester) or a random copoly(ester).

Whilst there is no specific intention to limit the mechanism of ring opening polymerization employed in the present invention and whilst therefore ring opening polymerization of cyclic monomers by the anionic route, via basic catalysts is not strictly precluded, it is preferred herein for said polymerization to proceed by a cationic route, via acid catalysis. Broadly, any suitable acidic ring opening polymerization catalyst may be utilized herein and, equally, mixtures of catalysts may be employed. Both Lewis and Brönsted acids may be suitable in this context, but the latter are preferred as they tend to be effective at temperatures of less than 150° C. and are usually effective at temperatures of from 50 to 100° C.

Examples of suitable Lewis acids include but are not limited to: $BF_3$; $AlCl_3$; $t\text{-BuCl/Et}_2AlCl$; $Cl_2/BCl_3$; $AlBr_3$;

AlBr$_3$.TiCl$_4$; I$_2$; SbCl$_5$; WCl$_6$; AlEt$_2$Cl; PF$_5$; VCl$_4$; AlEtCl$_2$; BF$_3$Et$_2$O; PCl$_5$; PCl$_3$; POCl$_3$; TiCl$_6$; and, SnCl$_4$.

Examples of Brönsted acid or proton acid type catalysts—which may optionally be disposed on solid, inorganic supports—include, but are not limited to: HCl; HBr; HI; H$_2$SO$_4$; HClO$_4$; para-toluenesulfonic acid; trifluoroacetic acid; and, perfluoroalkane sulfonic acids, such as trifluoromethane sulfonic acid (or triflic acid, CF$_3$SO$_3$H), C$_2$F$_5$SO$_3$H, C$_4$F$_9$SO$_3$H, C$_5$F$_{11}$SO$_3$H, C$_6$F$_{13}$SO$_3$H and C$_8$F$_{17}$SO$_3$H. The most preferred of these strong acids is trifluoromethane sulfonic acid (triflic acid, CF$_3$SO$_3$H).

The catalysts for said ring opening polymerization may usually be employed at a concentration of from 1 to 1000 ppm by weight based on the total weight of the monomers to be polymerized. Preferably from 5 to 150 ppm by weight are used, most preferably from 5 to 50 ppm. The catalytic amount may be reduced when the temperature at which the monomers and the catalyst are contacted is increased.

The ring opening polymerization may conveniently be carried out at a temperature in the range from 10 to 150° C. Preferably, however, the temperature range is from 20 or 50 to 100° C. as obviating high temperatures can limit the loss of volatile monomers from the reaction mixture due to their lower boiling point.

The process pressure is not critical. As such, the polymerization reaction can be run at sub-atmospheric, atmospheric, or super-atmospheric pressures but pressures at or above atmospheric pressure are preferred.

Importantly, the reaction should be performed under anhydrous conditions and in the absence of any compound having an active hydrogen atom. Exposure to atmospheric moisture may be avoided by providing the reaction vessel with an inert, dry gaseous blanket. Whilst dry nitrogen, helium and argon may be used as blanket gases, precaution should be used when common nitrogen gases are used as a blanket, because such nitrogen may not be dry enough on account of its susceptibility to moisture entrainment; the nitrogen may require an additional drying step before use herein.

The duration of the reaction is dependent on the time taken for the system to reach equilibrium. Equally, however, it is understood that the desired product can be obtained by stopping the equilibration at exactly the desired time: for example, the reaction can be monitored by analyzing viscosity over time or by analyzing monomer conversion using gas chromatography and the reaction stopped when the desired viscosity or monomer conversion is attained. These considerations aside, the polymerization reaction generally takes place for from 0.5 to 72 hours and more commonly from 1 to 30 or 1 to 20 hours. Acid catalysts present in the reaction mixture at the end of the polymerization reaction can easily be neutralized in order to stabilize the reaction product.

Upon completion of the polymerization, it is possible to remove any solid, suspended compounds by, for example, filtration, crossflow filtration or centrifugation. Further, the output of the polymerization may be worked up, using methods known in the art, to isolate and purify the hydroxyl-functionalized polyesters. Mention in this regard may be made of extraction, evaporation, distillation and chromatography as suitable techniques. Upon isolation, it has been found that typical yields of the hydroxyl-functionalized polyesters are at least 40% and often at least 60%.

The polyesters derived by this ring opening polymerization process may possess a molecular weight (Mn) as determined as measured by gel permeation chromatography (GPC) in tetrahydrofuran using a polystyrene standard, of at least 5000, preferably from 10000 to 200000 g/mol. Moreover, the polymers may be characterized by a polydispersity index in the range from 1.0 to 2.5, preferably from 1.0 to 2.0.

ii) Polyester Formation

In a second exemplary embodiment, the polymer (p-EFL) of the present invention may be used as a macro-monomer in an esterification, wherein the resultant copolymer comprises non-lactoyl units derived from at least two co-monomers which are capable of forming an ester bond. More particularly, those co-monomers comprise: i) at least one diol; and (ii) at least one dicarboxylic acid or its ester forming derivative.

Suitable diols (i) for use in this context include saturated and unsaturated aliphatic and cycloaliphatic dihydroxy compounds as well as aromatic dihydroxy compounds. These diols preferably have a molecular weight of 250 daltons or less. When used herein, the term "diol" should be construed to include equivalent ester forming derivatives thereof, provided, however, that the molecular weight requirement pertains to the diol only and not to its derivative. Exemplary ester forming derivatives include the acetates of the diols as well as, for example, ethylene oxide or ethylene carbonate for ethylene glycol.

Preferred diols are those having from 2 to 10 carbon atoms. As examples of these diols there might be mentioned: ethylene glycol; propylene glycol; 1,3-propane diol; 1,2-butane diol; 2-methyl propanediol; 1,3-butane diol; 1,4-butane diol; 2,3-butane diol; neopentyl glycol; hexanediol; decanediol; hexamethylene glycol; cyclohexane dimethanol; resorcinol; and hydroquinone. Mixtures of such diols may be employed, but in this regard, it is generally preferred that at least about 60 mol. % and preferably at least 80 mol. %, based on the total diol content, be the same diol.

In a preferred embodiment, the diol is selected from: ethylene glycol; propylene glycol; 1,3-propane diol; 1,2-butane diol; 1,3-butane diol; 1,4-butane diol; 2,3-butane diol; neopentyl glycol; hexamethylene glycol; cyclohexane dimethanol; and mixtures thereof. Most preferably, the diol is either ethylene glycol or neopentyl glycol.

Dicarboxylic acids (ii) which are suitable for use in the above context include aliphatic, cycloaliphatic, and/or aromatic dicarboxylic acids. These acids should preferably have molecular weight of less than 300 daltons. The term "dicarboxylic acids" as used herein includes equivalents of dicarboxylic acids having two functional carboxyl groups which perform substantially like dicarboxylic acids in reaction with glycols and diols in forming polyesters. These equivalents include esters and ester forming reactive derivatives, such as acid halides and anhydrides, provided however that the molecular weight preference mentioned above pertains to the acid and not to its equivalent ester or ester-forming derivatives. Thus, an ester of a dicarboxylic acid having a molecular weight greater than 300 daltons or an acid equivalent of a dicarboxylic acid having a molecular weight greater than 300 daltons are included provided the acid has a molecular weight below 300 daltons. Additionally, the dicarboxylic acids may contain any substituent groups(s) or combinations which do not substantially interfere with the polymer formation and use of the polymer of this invention.

Preferred dicarboxylic acids are those selected from the group comprising alkyl dicarboxylic acids having a total of 2 to 16 carbons atoms and aryl dicarboxylic acids having a total of from 8 to 16 carbon atoms. Representative alkyl dicarboxylic acids include: glutaric acid; adipic acid;

pimelic acid; succinic acid; sebacic acid; azelaic acid; and malonic acid. A preference for adipic acid might be mentioned here.

Representative aryl dicarboxylic acids include: terephthalic acid; phthalic acid; isophthalic acid; the dimethyl derivatives of said acids; and mixtures thereof.

Compositions Containing the Homo- and Co-Polymers (P-EFL) of the Present Invention The polymers (p-EFL) of the present invention are considered to be versatile and thereby have a plethora of uses. For example, the lactone bearing polymers can be used to prepare ionic complexes with agents—including therapeutic agents such as a peptide—having a cationic moiety. The lactone ring(s) present in these polymers can also be opened by an alkali hydroxide to form an alkali metal salt of the corresponding hydroxycarboxylic acid. Furthermore, polymers containing lactone groups can be crosslinked by means of multifunctional compounds that can react with lactone. Multifunctional amines are particularly desirable in this regard.

It is anticipated that the functionalized polymers of the present invention per se may find utility as a curable, crosslinkable or otherwise reactive component of a coating composition, a sealant composition or an adhesive composition.

In an important embodiment of the present invention, there is provided a composition having two separate, reactive components that when mixed together form a reactive mixture that undergoes curing or hardening, said two-component composition comprising:

in a first component, said polymer (p-EFL); and, in a second component, an un-substituted or hydroxyl-substituted mono-, di- or trialkylamines.

Preferably, the alkylamines are at least one of a primary amine and a secondary amine. More preferably the alkylamine is a primary amine. Independently or additionally, it is preferred that the said second component comprises an un-substituted or hydroxyl-substituted mono-, di- or tri-($C_1$-$C_{12}$) alkylamine. Further, again independently of or additionally to these preferred conditions, the composition may be characterized in that the molar ratio of lactone groups in component (i) to amine groups in component (ii) is in the range from 0.8:1 to 2.5:1.

Suitable examples of alkylamines in component (ii) include but are limited to: methyl-, dimethyl- or trimethyl-amine; ethyl-, diethyl- or triethyl-amine; ethanol-, diethanol- or triethanol-amine; tris-(hydroxymethyl)-methylamine; 2-hydroxy-tert-butylamines; N,N-dimethyl-N-(2-hydroxy-ethyl)-amine; N-methyl-D-glucamine; diisopropylethylamine; and ethyldiisopropylamine.

Said compositions—such as a coating, sealant or adhesive composition—comprising homo- or copolymers (p-EFL) obtained in the present invention will typically further comprise adjuvants and additives that can impart improved properties to these compositions. For instance, the adjuvants and additives may impart one or more of: improved elastic properties; improved elastic recovery; longer enabled processing time; faster curing time; and lower residual tack. Included among such adjuvants and additives are catalysts, plasticizers, stabilizers, antioxidants, fillers, reactive diluents, drying agents, adhesion promoters and UV stabilizers, fungicides, flame retardants, rheological adjuvants, color pigments or color pastes, and/or optionally also, to a small extent, solvents.

A "plasticizer" for the purposes of this invention is a substance that decreases the viscosity of the composition and thus facilitates its processability. Herein the plasticizer may constitute up to 40 wt. % or up to 20 wt. %, based on the total weight of the composition, and is preferably selected from the group consisting of: polydimethylsiloxanes (PDMS); diurethanes; ethers of monofunctional, linear or branched C4-C16 alcohols, such as Cetiol OE (obtainable from Cognis Deutschland GmbH, Düsseldorf); esters of abietic acid, butyric acid, thiobutyric acid, acetic acid, propionic acid esters and citric acid; esters based on nitrocellulose and polyvinyl acetate; fatty acid esters; dicarboxylic acid esters; esters of OH-group-carrying or epoxidized fatty acids; glycolic acid esters; benzoic acid esters; phosphoric acid esters; sulfonic acid esters; trimellitic acid esters; epoxidized plasticizers; polyether plasticizers, such as end-capped polyethylene or polypropylene glycols; polystyrene; hydrocarbon plasticizers; chlorinated paraffin; and, mixtures thereof. It is noted that, in principle, phthalic acid esters can be used as the plasticizer but these are not preferred due to their toxicological potential. It is preferred that the plasticizer comprises or consists of one or more polydimethylsiloxane (PDMS).

"Stabilizers" for purposes of this invention are to be understood as antioxidants, UV stabilizers or hydrolysis stabilizers. Herein stabilizers may constitute in toto up to 10 wt. % or up to 5 wt. %, based on the total weight of the composition. Standard commercial examples of stabilizers suitable for use herein include: sterically hindered phenols; thioethers; benzotriazoles; benzophenones; benzoates; cyanoacrylates; acrylates; amines of the hindered amine light stabilizer (HALS) type; phosphorus; sulfur; and, mixtures thereof.

As noted, the compositions according to the present invention can additionally contain fillers. Suitable here are, for example, chalk, lime powder, precipitated and/or pyrogenic silicic acid, zeolites, bentonites, magnesium carbonate, diatomite, alumina, clay, talc, titanium oxide, iron oxide, zinc oxide, sand, quartz, flint, mica, glass powder, and other ground mineral substances. Organic fillers can also be used, in particular carbon black, graphite, wood fibers, wood flour, sawdust, cellulose, cotton, pulp, cotton, wood chips, chopped straw, chaff, ground walnut shells, and other chopped fibers. Short fibers such as glass fibers, glass filament, polyacrylonitrile, carbon fibers, Kevlar fibers, or polyethylene fibers can also be added. Aluminum powder is likewise suitable as a filler.

The pyrogenic and/or precipitated silicic acids advantageously have a BET surface area from 10 to 90 $m^2/g$. When they are used, they do not cause any additional increase in the viscosity of the composition according to the present invention but do contribute to strengthening the cured composition.

It is likewise conceivable to use pyrogenic and/or precipitated silicic acids having a higher BET surface area, advantageously from 100 to 250 $m^2/g$, in particular from 110 to 170 $m^2/g$, as a filler: because of the greater BET surface area, the effect of strengthening the cured composition is achieved with a smaller proportion by weight of silicic acid.

Also suitable as fillers are hollow spheres having a mineral shell or a plastic shell. These can be, for example, hollow glass spheres that are obtainable commercially under the trade names Glass Bubbles®. Plastic-based hollow spheres, such as Expancel® or Dualite®, may be used and are described in EP 0 520 426 B1: they are made up of inorganic or organic substances and each have a diameter of 1 mm or less, preferably 500 µm or less.

Fillers which impart thixotropy to the composition may be preferred for many applications: such fillers are also described as rheological adjuvants, e.g., hydrogenated castor oil, fatty acid amides, or swellable plastics such as PVC.

The total amount of fillers present in the compositions of the present invention will preferably be from 1 to 80 wt. %, and more preferably from 5 to 60 wt. %, based on the total weight of the composition. The desired viscosity of the curable composition will typically be determinative of the total amount of filler added and it is submitted that in order to be readily extrudable out of a suitable dispensing apparatus—such as a tube—the curable compositions should possess a viscosity of from 3000 to 150,000, preferably from 40,000 to 80,000 mPas, or even from 50,000 to 60,000 mPas.

Examples of suitable pigments are titanium dioxide, iron oxides, or carbon black.

In order to enhance shelf life even further, it is often advisable to further stabilize the compositions of the present invention with respect to moisture penetration through using drying agents. A need also occasionally exists to lower the viscosity of an adhesive or sealant composition according to the present invention for specific applications, by using reactive diluent(s). The total amount of reactive diluents present will typically be up to 15 wt. %, and preferably from 1 and 5 wt. %, based on the total weight of the composition.

The following examples are illustrative of the present invention and are not intended to limit the scope of the invention in any way.

EXAMPLES

The following materials were employed in the Examples:
α-angelica lactone: 4-Hydroxy-3-pentenoic acid γ-lactone, available from Sigma Aldrich
Triisopropyl orthoformate: CAS Number 4447-60-3, available from Sigma AldrichTriethyl orthoformate: CAS Number 122-51-0, available from Sigma Aldrich
Trimethyl orthoformate: CAS Number 149-73-5, available from Sigma Aldrich
Tributyl orthoformate: CAS Number 588-43-2, available from Sigma Aldrich
Tripropoxy orthoformate: CAS Number 621-76-1, available from Sigma Aldrich
Diethyl vinyl orthoformate: CAS Number 34712-46-4, available from Sigma Aldrich
Trioctadecyl orthoformate: CAS Number 17671-28-2, available from Sigma Aldrich
Tripentyl orthoformate: CAS Number 637-42-3, available from Sigma Aldrich

Example 1: Synthesis of 2-ethoxymethylene-α-angelica Lactone (EtOMAL)

179 mL of triethyl orthoformate (1.07 mol) were firstly added to 203 mL of acetic anhydride (2.15 mol) into a 1 L round bottom flask under argon atmosphere and under stirring. 64.4 mL of α-angelica lactone (0.72 mol) and 150 mg of 2,6-di-tert-butyl-p-cresol (BHT) were then added into the flask under argon atmosphere. The mixture was stirred under reflux conditions (T=110° C.-130° C.) and under an argon atmosphere for around 7 hours.

Five samples were withdrawn during the reaction at respectively 0, 60, 120, 260 and 410 minutes. Between 100 and 250 μL of these samples were added into chromatography (GC) vials containing 30 μL of dodecane used as the internal standard; 1.6 mL of toluene was added into all GC vials and the obtained solutions were analyzed by GC-FID. The relative amount of α-angelica lactone was calculated by the ratio between the integration areas normalized with respect to the internal standard and with respect to the amount of reaction mixture used for GC analysis.

Upon completion of the reaction, the mixture was brought to room temperature and it was stored overnight under argon atmosphere. Subsequently the mixture was distilled under vacuum.

77.25 g of a fraction containing the desired product EtOMAL were collected—at a temperature of approximately 120° C. and a pressure of 0.4 mbar—as a yellow liquid. GC-FID analysis indicated that this fraction contained around 90% of EtOMAL (Yield=61%). 25 mL of diethyl ether and 20 mL of hexane were added to the collected fraction under an argon atmosphere. The mixture was immersed in an ethanol bath and the temperature was slowly decreased by addition of dry ice into the bath. A white crystalline material precipitated and the latter was filtered under atmospheric conditions and washed several times with pentane. Finally, the product was dried overnight under vacuum and stored under inert conditions. The overall yield was about 40%.

The product was characterized by Nuclear Magnetic Resonance (NMR) as follows:

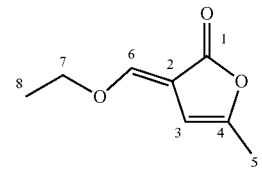

$^1$H NMR (300 MHz, CD$_2$Cl$_2$, δ): =7.18 (q, $^6$J=0.75 Hz, H6, 1H), 5.80 (m, H3, 1H), 4.16 (q, $^3$J=7.05 Hz, H7, 2H), 2.04 (dd, $^4$J=1.44 Hz, $^6$J=0.75 Hz, H5, 3H), 1.34 (t, $^3$J=7.07 Hz, H8, 3H) ppm.

$^{13}$C NMR (100 MHz, CD$_2$Cl$_2$, δ): 171.06 (C1), 154.17 (C6), 151.54 (C4), 107.86 (C2), 99.22 (C3), 71.93 (C7), 15.42 (C8), 14.31 (C5) ppm.

Example 2: Anionic Polymerization of EtOMAL

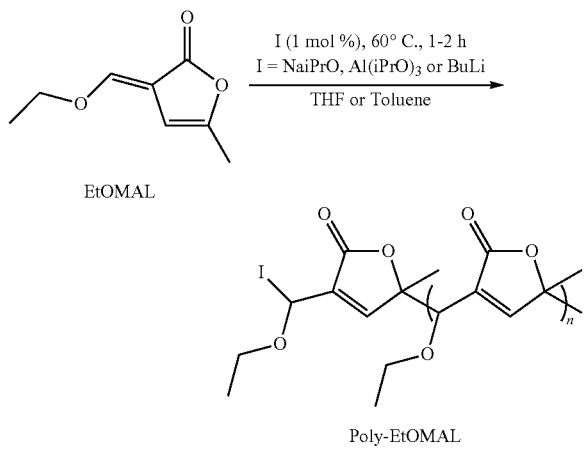

Example 2.1: Synthesis and Characterization of Poly-EtOMAL Using Sodium Isopropoxide (NaiPrO) as the Catalyst

2.1.1 Synthesis 800 mg of EtOMAL was dissolved in 1 mL of toluene under inert conditions. The solution was added to a mixture of 4 mg of NaiPrO and 1 mL of toluene at 60° C. under an inert atmosphere. Additional toluene (1 mL) was used to quantitatively transfer EtOMAL into the reaction mixture.

Shortly after the addition of EtOMAL a solid material in the form of a gel started to precipitate. The reaction was left for 2 hours at 60° C. Afterwards around 1 mL of an aqueous HCl (0.1 M) solution was added into the reaction Schlenk vessel. The solid was then washed several times with toluene. Afterwards the washed solid was dissolved in dichloromethane and filtered through a short column of $SiO_2$. Finally, it was dried overnight under vacuum. Overall yield was typically higher than 90%.

2.1.2 NMR Characterization of Poly-EtOMAL

The product was characterized by Nuclear Magnetic Resonance (NMR) as follows:

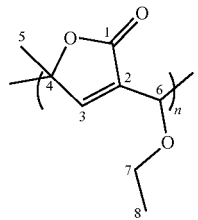

$^1$H NMR (300 MHz, $CD_2Cl_2$, δ): =7.43 (bs, $H_3$, 1H), 4.29 (bs, $H_6$, 1H), 3.43 (bs, $H_7$, 2H), 1.45 (bs, $H_5$, 3H), 1.13 (bs, $H_8$, 3H) ppm.

$^{13}$C NMR (75 MHz, $CD_2Cl_2$, δ): 171.35 ($C_1$), 156.22 ($C_3$), 131.78 ($C_2$), 88.17 ($C_4$), 76.80 ($C_6$), 66.77 ($C_7$), 20.79 ($C_5$), 15.27 ($C_8$) ppm.

2.1.3 Molecular Weight Characterization of poly-EtOMAL

Example 2.2: Synthesis of Poly-EtOMAL by Using aluminum Isopropoxide [Al[iPrO]$_3$] as the Catalyst 900 mg of EtOMAL were dissolved in 1 mL of toluene under inert conditions. The solution was added to Al(iPrO)$_3$ (1o mol. %) in 1 mL of toluene at 60° C. under an inert atmosphere. Additional toluene (1-3 mL) was used to quantitatively transfer EtOMAL into the reaction mixture.

Shortly after the addition of EtOMAL a solid material in the form of a gel started to precipitate. The reaction was left for 2 h at 60° C. Afterwards aqueous HCl (0.1 M) solutions were used to quench the reactions. The solid was washed on a Bruckner filter several times with toluene, dichloromethane and diethyl ether. Finally, it was dried overnight under vacuum. Overall yield was typically higher than 80%. Polymer formation was identified by NMR analysis.

Example 2.3: Synthesis of Poly-EtOMAL by Using Butyl Lithium as the Catalyst 170 mg of EtOMAL was dissolved in 2 mL of THF under inert conditions. The solution was heated to reach 60° C. under an inert atmosphere. A volume of BuLi 1.6 M solution in hexane corresponding to 1 mol % vs. EtOMAL was then added under stirring to the monomer solution. The reaction was quenched after 1 hour with aqueous HCl (1 M) solutions. Afterwards dichloromethane was added to the mixture and the obtained solution was filtered through celite. Finally, it was dried overnight under vacuum. Polymer formation was identified by NMR analysis.

Example 3: Synthesis of 2-isopropoxymethylene-α-angelica Lactone ($^i$PrOMAL)

Triisopropyl orthoformate (61.1 g, 321 mmol) was reacted with α-angelica lactone (21.2 g, 216 mmol) under reflux conditions for 7 hours in the presence of acetic anhydride (65.8 g, 645 mmol) and 2,6-di-tert-butyl-p-cresol (BHT, 0.060 g, 0.27 mmol).

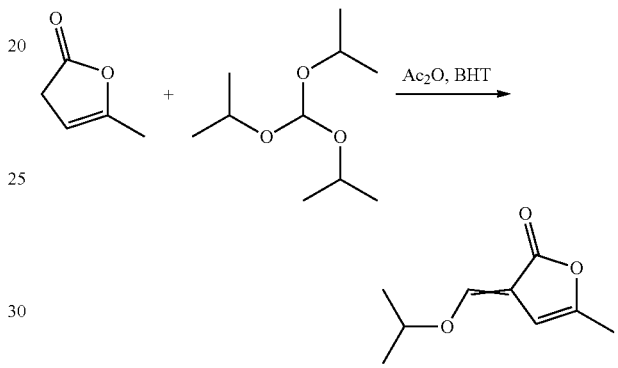

Five fractional samples of the reaction mixture were withdrawn during the reaction and added into gas chromatography (GC) vials containing 30 μL of dodecane used as the internal standard; 1.6 mL of toluene was added into all GC vials and the obtained solutions were analyzed by GC-FID. The relative amount of α-angelica lactone was calculated by the ratio between the integration areas normalized with respect to the internal standard and with respect to the amount of reaction mixture used for GC analysis.

Upon completion of the reaction, the reaction mixture was distilled under reduced pressure to obtain $^i$PrOMAL as a light-yellow oil (12.1 g, 33.3% yield), which product was characterized as follows:

$^1$H NMR (400 MHz, CDCl$_3$) δ 7.22 (s, 1H), 5.78 (s, 1H), 4.28 (sep, J=4 Hz, 1H), 2.03 (s, 3H), 1.31 (d, 6H) ppm.

$^{13}$C NMR (100 MHz, CDCl$_3$) δ 171.5, 153.3, 151.2, 107.9, 33.5, 79.5, 22.1, 14.5 ppm.

Example 4: Further Syntheses

The above method for the synthesis of 2-isopropoxymethylene-α-angelica lactone ($^i$PrOMAL) was viably repeated at yields≥25% using the following orthoformates ((XO)$_3$CH): trimethyl orthoformate ($R^1$=$R^2$=$R^3$=Me); tributyl orthoformate ($R^1$=$R^2$=$R^3$=Bu); tripropyl orthoformate ($R^1$=$R^2$=$R^3$=nPr); diethyl vinyl orthoformate ($R^1$=$R^2$=Et, $R^3$=$CH_2$=$CH_2$); trioctadecyl orthoformate ($R^1$=$R^2$=$R^3$=$C_{18}H_{37}$); and, tripentyl orthoformate ($R^1$=$R^2$=$R^3$=$C_5H_{11}$).

In view of the foregoing description and examples, it will be apparent to those skilled in the art that equivalent modifications thereof can be made without departing from the scope of the claims.

What is claimed is:

1. A monomer for chain-growth polymerization, having the general formula:

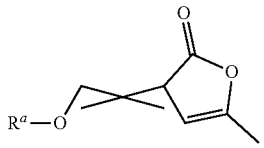

wherein: $R^a$ is a $C_3$-$C_{30}$ cycloalkyl or $C_2$-$C_{12}$ alkenyl group.

2. The monomer of claim 1, wherein $R^a$ is a $C_2$-$C_8$ alkenyl group.

3. A method of synthesis of the monomer of claim 1, the method comprising reacting, in the presence of an acid anhydride and an antioxidant:
at least one α-angelica lactone; and
at least one orthoester having the general formula (1):

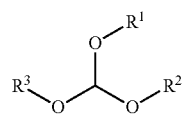

wherein $R^1$, $R^2$ and $R^3$ are independently selected from $C_3$-$C_{30}$ cycloalkyl or $C_2$-$C_{12}$ alkenyl groups.

4. The method of claim 3, wherein the acid anhydride is selected from the group consisting of acetic anhydride, propionic anhydride, butyric anhydride, and succinic anhydride.

5. The method of claim 3, wherein the antioxidant is at least one sterically hindered phenol.

6. A method of chain growth polymerization of at least one monomer of claim 1,
wherein the chain growth polymerization is conducted in the presence of an initiator selected from the group consisting of alkali metal organyls, alkali metal alkoxides, alkali metal thiolate, and alkali metal amides.

7. The method of claim 6, wherein the initiator is present in an amount of from 0.0001 to 5 wt. %, based on the total weight of the at least one monomer.

8. The method of claim 6, wherein the initiator is an alkali metal alkoxide wherein the alkali metal alkoxide is selected from the group consisting of aliphatic alkoxides of lithium, sodium, and potassium.

9. The method of claim 6, wherein the initiator is an alkali metal organyl, wherein the alkali metal organyl is an organolithium compound selected from the group consisting of ethyllithium, propyllithium, isopropyllithium, n-butyllithium, sec-butyllithium, tert-butyllithium, phenyllithium, diphenylhexyllithium, hexamethylenedilithium, butadienyllithium, isoprenyllithium, polystyryllithium, 1,4-dilithiobutane, 1,4-dilithio-2-butene, and 1,4-dilithiobenzene and any combination thereof.

10. The method of claim 6, wherein the chain growth polymerization is of a monomer mixture, wherein the monomer mixture comprises:
the monomer of claim 1 in an amount of from 15 to 75 wt. %; and
at least on co-monomer in an amount of from 25 to 85 wt%, wherein the amounts are based on the total weights of the monomers in the monomer mixture.

11. The method of claim 4, wherein the acid anhydride is present in a catalytic amount based on the total number of moles of the reactants.

12. The method of claim 5, wherein the antioxidant is present in an amount greater than 0 and up to 10 wt %, based on the total weight of the reactants.

13. The method of claim 10, wherein the at least one co-monomer is selected from the group consisting of (meth) acrylonitrile, alkyl (meth)acrylate esters, (meth)acrylic acids, vinyl esters, and vinyl monomers.

14. The method of claim 10, wherein the at least one co-monomer is a vinyl monomer selected from the group consisting of 1,3-butadiene, isoprene, styrene, divinyl benzene, heterocyclic vinyl compounds, and vinyl halides.

15. A composition comprising:
the monomer of claim 1; and
at least one co-monomer selected from the group consisting of (meth)acrylonitrile, alkyl (meth) acrylate esters, (meth)acrylic acids, vinyl esters, and vinyl monomers.

16. A composition comprising:
a monomer having the general formula:

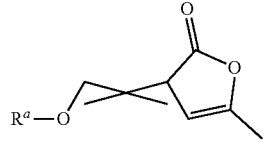

wherein $R^a$ is selected from the group consisting of a $C_1$-$C_{30}$ alkyl, $C_3$-$C_{30}$ cycloalkyl, $C_6$-$C_{18}$ aryl, and $C_2$-$C_{12}$ alkenyl group; and
at least one co-monomer.

17. The composition of claim 16, wherein the least one co-monomer is selected from the group consisting of (meth) acrylonitrile, alkyl (meth) acrylate esters, (meth)acrylic acids, vinyl esters, and vinyl monomers.

* * * * *